(12) United States Patent
Engelbrecht

(10) Patent No.: US 7,090,498 B2
(45) Date of Patent: Aug. 15, 2006

(54) ADHESIVE SILICON FILLING AND FIXING MATERIALS

(75) Inventor: Juergen Engelbrecht, Hamburg (DE)

(73) Assignee: S&C Polymer Silicon- und Composite-Spezialitaten GmbH, Elmshorn (DE)

( * ) Notice: Subject to any disclaimer, the term of this patent is extended or adjusted under 35 U.S.C. 154(b) by 0 days.

(21) Appl. No.: 10/343,885

(22) PCT Filed: Aug. 6, 2001

(86) PCT No.: PCT/EP01/09071

§ 371 (c)(1),
(2), (4) Date: Jun. 9, 2003

(87) PCT Pub. No.: WO02/11680

PCT Pub. Date: Feb. 14, 2002

(65) Prior Publication Data

US 2004/0044164 A1    Mar. 4, 2004

(30) Foreign Application Priority Data

Aug. 7, 2000 (DE) .............................. 100 39 297
Aug. 17, 2000 (DE) .............................. 100 40 725

(51) Int. Cl.
*A61C 5/00* (2006.01)

(52) U.S. Cl. .............................. 433/217.1; 433/228.1; 528/15; 528/31; 523/109; 523/116; 523/118

(58) Field of Classification Search .................. 528/15, 528/31; 433/228.1, 217.1; 523/109, 116, 523/118
See application file for complete search history.

(56) References Cited

U.S. PATENT DOCUMENTS

| 3,127,363 A |   | 3/1964  | Nitzsche |        |
|-------------|---|---------|----------|--------|
| 5,476,912 A | * | 12/1995 | Hosoi et al. | 526/279 |
| 5,696,211 A | * | 12/1997 | Chung et al. | 525/478 |
| 6,599,974 B1 | * | 7/2003 | Bublewitz et al. | 524/588 |
| 6,612,836 B1 | * | 9/2003 | Engelbrecht | 433/37 |

FOREIGN PATENT DOCUMENTS

| EP | 0 632 060 A   | 1/1995 |
| EP | 0 864 312 A   | 9/1998 |
| WO | WO 99/03424 A | 1/1999 |

OTHER PUBLICATIONS

DE 198 52 056 A 1 (abstract) May 2000.*

* cited by examiner

*Primary Examiner*—Margaret G. Moore
(74) *Attorney, Agent, or Firm*—Frommer Lawrence & Haug LLP; Ronald R. Santucci

(57) ABSTRACT

This invention relates to the kit of parts containing (co) polymers having hydrogen-siloxane groups, a catalyst, a vinyl compound and a hydrosilyl compound. The kits of parts may be used as permanent or temporary, soft or hard elastic, bonding or filling materials on a dental substrate or a bone substrate.

12 Claims, No Drawings

ADHESIVE SILICON FILLING AND FIXING MATERIALS

This application is a 371 of PCT/EP01/09071 filed on Aug. 6, 2001, published on Feb. 14, 2002 under publication number WO 02/11680 A1 which claims priority benefits from German patent application number DE 100 39 297.0 filed Aug. 7, 2000 and German patent application number DE 10040 725.0 filed Aug. 17, 2000.

This invention relates to the kits of parts containing (co)polymers having hydrogen-siloxane groups, a catalyst, a vinyl compound and a hydrosilyl compound. These kits of parts may be used as permanent or temporary bonding or filling materials, either soft elastic or hard elastic, on dental or bone substrate.

Silicones are often used as impression molding compounds in the field of dentistry. In particular, condensation-crosslinking polysiloxanes containing hydroxyl groups (e.g., crosslinked by orthosilicates $Si(OR)_4$ or silanes $RSi(OR)_3$) or addition-crosslinking polysiloxanes containing vinyl groups (crosslinked by polysiloxanes containing hydrosilyl groups) may be used. However, these materials are hardly known or used in the area of dental filling materials or cements.

German Patent 3 915 592 describes a dental cement consisting of a silicone oil which contains acid groups and is modified with carboxyl groups. Blending with metal oxides or metal hydroxides leads to a hard filling material that resembles cement, especially for filling and sealing a dental root canal.

U.S. Pat. No. 3,082,520 A discloses a mixture for filling dental root canals, based on a polysiloxane containing hydroxyl groups crosslinked with organotriacyloxysilane. This type of condensation-crosslinking silicone results in cleavage of acetic acid and results in shrinkage, which is a disadvantage for filling materials. A similar method is described by U.S. Pat. No. 3,127,363 A, which also discloses a condensation-crosslinking silicone system.

German Patent 197 09 531 describes an addition-crosslinking polysiloxane system for filling root canals, having the advantage of lower shrinkage in comparison with the materials according to the previous patent applications.

However, all the preceding formulations have one very major disadvantage: they do not adhere to a dental substrate or a bone substrate.

PCT/EP 00/01042 and European Patent 0 632 060 A1 describe adhesives comprising copolymers containing hydrogen-siloxane groups and solutions thereof which result in adhesion of addition-crosslinking silicones to prosthetic material, for example.

In both these patent publications, copolymers which contain, for example, fragments of polymerized methacrylates and fragments of hydrosilyl-containing polysiloxanes produce the effect of adhesion to the plastic, which is solubilized at the surface, and to the addition-crosslinking silicone.

Unexpectedly, the adhesives of PCT/EP 0001042 will also adhere to hard dental substance.

The object of the present invention was to discover mixtures that would be capable of adhering to dental substrate or bone substrate and could be used as soft or hard elastic adhesive cement or as filling materials.

According to this invention, this object is achieved by using a kits of parts which contains
  a) a (co)polymer having hydrogen-siloxane groups,
  b) a catalyst,
  c) a vinyl compound, and
  d) a hydrosilyl compound.

Such a kits of parts may be used to produce permanent or temporary, soft or hard elastic adhesive cements or filling materials for use on dental or bone substrate.

The kit of parts preferably consists of two sub-kits of parts, whereby sub-kit of parts 1 contains
  a) the (co)polymer having hydrogen-siloxane groups, and sub-kit of parts 2 contains
  b) the catalyst,
  c) the vinyl compound and
  d) the hydrosilyl compound.

Sub-kit of parts 1 (also referred to as "the primer") contains as an important substance that adheres to dental and bone substrate (co)polymers, i.e., polymers or copolymers, also referred to below as simply polymers, which have hydrogen-siloxane groups. The basic structure of these polymers may be, for example, that of copolymers of methyl methacrylate and allyl methacrylate onto which hydrogen-siloxane has been grafted. They may also be copolymers such as those described in detail in European Patent 0 632 060 A1 or, especially preferably, copolymers obtained by direct polymerization of hydrogen-siloxanes such as those described in PCT/EP 0001042 and in Japanese unexamined patent specification HEI 10-25322.

The SiH groups of the hydrogen-siloxane units are evidently capable of reacting with the POH groups of apatite of dental substance so that bonding of the latter to the dental substance comes about by chemical methods without prior mechanical roughening (etching).

In addition, the primers used according to this invention may also contain up to 10 parts by weight, preferably up to 1 part by weight of a vinyl compound, up to 500 ppm, preferably up to 50 ppm platinum catalyst and up to 80 parts by weight, preferably up to 20 parts by weight polymer(s) without hydrogen-siloxane groups.

In addition, however, it is also possible to add up to 3 parts by weight, preferably up to 0.3 parts by weight of hydrogen polysiloxanes that are used in addition-crosslinking silicones.

It may optionally be beneficial to add a catalyst which is capable of catalyzing the reactions of SiH+POH or SiH+vinylsiloxane. Possible catalysts include the compounds of platinum or palladium as well as alloys thereof.

Especially suitable catalysts are platinum(0) compounds which are prepared by starting with platinum hexachloroplatinate and are conventionally used in systems of addition-crosslinking vinylpolysiloxanes/hydrogen polysiloxanes. Examples of such catalysts include the $Pt_x(divinyltetramethyldisiloxane)_y$ of platinum(0).

The vinyl compounds which are added if necessary should preferably be divinyl compounds. However, compounds having more than two vinyl groups may also be appropriate, e.g., when a high degree of crosslinking is to be achieved. Preferred divinyl compounds include divinyl ethers such as divinyl ether of triethylene glycol or cyclohexanediol or divinylpolysiloxanes such as those used in addition-crosslinking silicones or divinyltetramethyldisiloxane. It may also be advantageous to add methacrylate compounds.

Compounds having vinyl groups may optionally also have in an advantageous manner acid groups which may additionally contribute to adhesion to dental substance or bone substance. Examples of such acid groups include COOH, phosphate and phosphonate.

Other hydrogen-siloxanes which may optionally also be added preferably include polysiloxanes having at least two SiH groups, preferably three SiH groups.

In addition, primers used according to this invention may also contain polymers which do not have any SiH groups. Examples include polymethacrylates, polycarbonates, polyesters and similar polymers, if they are soluble in the mixture and compatible with the system.

Likewise, mixtures according to this invention may also contain readily volatile solvents, which make it possible to apply the lacquer in the form of a very thin film. Suitable solvents include especially volatile inert solvents such as halogenated or non-halogenated aliphatic or aromatic hydrocarbons, ethers, ketones, esters or cyclic siloxanes.

Compounds or agents which have biocidal or pharmaceutical effects such as antibacterial or anti-inflammatory effects may also be added. Biocidal compounds or agents kill bacteria, viruses and/or fungi, while biostatic compounds or agents inhibit the growth of bacteria, viruses and/or fungi.

The mixtures to be cured (sub-kit of parts 2), which are used in a second step after application of the adhesive primer, include addition-crosslinking silicones whose basic components include vinyl compounds and hydrosilyl compounds plus catalysts. They may contain fillers, thixotroping agents, thickeners, pigments, coloring agents, plasticizers, stabilizers, emulsifiers, hydrophobing agents, biocidal or pharmaceutical additives. These additives depend on the properties of the bonding or filling material to be achieved. For example, it is possible to achieve a high hardness due to the use of fillers such as finely divided powders of quartz, calcium carbonate, talc, etc., such as those also used in addition-crosslinking mold-casting silicones. Thixotroping agents such as pyrogenic silicas or ethylcellulose, which control the flow properties or the tensile strength, pigments or coloring agents which make the appearance more closely resemble teeth or bone, plasticizers, stabilizers, emulsifiers and hydrophilic agents, such as those which ensure proper handling and stability properties, as well as biocidal or pharmaceutical additives, which take into account the special biological environment of dental and bone substance, may also be used.

The catalysts used in sub-kits of parts 2 are preferably platinum catalysts, and the vinyl compounds are preferably vinylsiloxane compounds. The hydrosilyl compounds are preferably hydrogen-siloxane compounds.

The kits of parts according to this invention consisting of the abovementioned primers and curing mixtures are excellently suitable as soft or hard elastic sealing materials to adhere to dental or bone substance. The type of soft or hard elasticity may be adjusted through the final curing mixture, as may also the viscoelastic properties or curing times. It may be advantageous to adjust the curing mixtures to yield kneadable materials, so that in the case of temporary filling of a dental cavity, for example, a tooth-colored mixture of addition-crosslinking silicone kneading stock can be pressed into the cavity after being kneaded together after application of the primer and allowed to cure there while the patient bites down to form a hard elastic filling. However, it may also be advantageous to have a low-viscosity tooth-colored mixture flow directly from a self-mixing dual-cartridge applicator into a cavity pretreated with the primer, to seal it with a prefabricated occlusion matrix of thermoplastic film, for example, and to allow it to cure. The hardness may be the same as that of the kneadable application form. The fillings remain in the cavity due to the adhesive effect of the primer. Without application of the adhesive primer, cracks rapidly develop in the edge due to the elastic movements in chewing. Apart from the problems of contamination in the edge gaps, the filling will quickly fall out again in the absence of the adhesive primer.

The adhesive power of the primer may be adjusted in advance. The adhesive power of the primer is higher or lower depending on the number of SiH adhesive groups on the copolymer. The adhesive power may also be reduced by using only spot application of adhesive or by not coating all surfaces.

Temporary fillings applied with a primer of a reduced adhesive power and used with curing mixtures of the type according to this invention are inexpensive, quick to apply and may also be applied in an emergency outside of the usual dental office chair environment. They adhere adequately well to prevent them from falling out spontaneously and they can be removed again easily with a hand instrument.

In the case of root canal fillings based on addition-crosslinking silicones, the additional use of the adhesive primer may also durably support the essentially good sealing property to advantage.

In cases when it is necessary to restore missing bone substance without the requirements of high hardness and supporting effect, it may be advisable for them to have a permanent elasticity.

In particular, when it is necessary to fill or open a bone cavity, the application of adhesive primer and the curable silicone mixture according to this invention may result in embodiments that could not be achieved in the past. In another application, bone parts subject to pressure may be buffered with silicone, even on a temporary basis.

The applications according to this invention may also be used to develop new applications as elastic bonding materials.

Thus, inlays or onlays made of metal, ceramic or glass-filled methacrylate composites may be cemented in a load-bearing manner to dentin and dental enamel with a durable hard elastic bond with the help of curing vinyl silicones after silanization of the surfaces of the inlays/onlays with activated silanes such as $RSi(OH)_3$ (R=methyl, ethyl, vinyl, methacryl, allyl) and application of the adhesive primer to dentin and dental enamel in the cavity area. The elasticity of the cement allows buffering of stresses due to occlusal peak loading of the onlay/inlay surfaces. New possibilities are available in particular due to the freedom from edge gaps because of the use of these extremely low-shrinkage addition-crosslinking silicones.

Use as a bracket adhesive for orthodontic regulation of tooth positions also yields new possibilities: due to the adhesiveness of the primer to dentin and to non-noble metal brackets, a layer of elastic silicone cement between the tooth and the bracket may yield a gentler transfer of the tension force of the stretched tension bands of the bracket system to the teeth to be positioned.

The same thing is true of the primers used according to this invention and the curing mixtures as a cement for splints as a retention apparatus for paradontally damaged and loosened teeth. The use according to this invention permits a retention aid for adjacent teeth but does not apply a load to them in the same way as the supported tooth.

Especially new options are provided by the applications of primer and curing mixtures according to this invention as elastic bone cement. Thus, applications of a primer according to this invention to a bone part and to a layer of fragments ranging from millimeters to a few millimeters in size, optionally up to a few centimeters, permits an elastic connection between two bone parts. The use of primer and curing mixtures according to this invention may thus optionally assume the function of cartilage. The good bioavailability of addition-crosslinking silicones is known and is thus suitable in principle for such a purpose.

Elastic bonding of ceramic and bone is also possible in this way. The primers used for the application according to this invention may also adhere well to ceramic which contains sufficient SiO groups on the surface and can react excellently with the SiH groups of the primer. Thus, bioceramic joints may optionally be buffered by an intermediate layer of silicone, if necessary, and thus do not have such a high tendency to fracture, even under shock stresses.

EXAMPLES

Example 1

Temporary Dental Filling

If a gold inlay falls out of a tooth cavity in a situation in which a dentist is not available, the kits of parts according to this invention may be used even by a layperson. A quantity of Formasil A putty, an addition-crosslinking silicone impression casting compound (Kulzer, Australia, color of material approximately beige) included in the kit and a colorless primer according to Example 2 of PCT/EP 00/01042, which is also included in the kit and also contains as the adhesive substance a polymer product of hydrogensiloxane and ethyl methacrylate, may serve as a temporary filling. After rinsing with water and drying with small pieces of a paper towel, the empty cavity is also wetted with the primer, likewise using small pieces of paper towel and a toothpick, and is left to dry (the solvent of the primer evaporates quickly). A small amount of prepared Formasil A putty is cautiously pressed into the cavity, a piece of plastic film (from the packing film for the paper towels) is placed between the opposing jaw and the silicone filling and then the jaw is closed and moved gently back and forth. The filling is fully cured after three minutes. Any overhanging material can easily be removed with the help of a finger or a toothpick. The temporary filling remains adhering in the cavity. It is hermetically sealed and the user can forget about it again immediately. After a few days, the temporary filling can be broken up easily by a dentist using a hand instrument and removed completely with the help of a rotating instrument. The cavity can then be treated by the dentist in an expert manner.

Example 2

Non-adhesive Root Canal Cement with Silicone (Not According to This Invention)

For a temporary closure, Guttapercha tips together with the root filling material RoekoSeal (Roeko, Germany), formulated on the basis of addition-crosslinking vinyl silicones introduced into an opened root canal and the cavity is sealed temporarily with Cavit, a temporary cement (Espe, Germany). After 10 days, the Cavit is removed. The gutta-percha tip may also be removed easily in one piece together with the RoekoSeal. The root canal can then be inspected and again sealed either temporarily or permanently.

Example 3

Adhering Root Canal Cement with Silicone

For a permanent seal, the root canal is rinsed with the adhesive primer solution as described in Example 1 before being sealed with gutta-percha from RoekoSeal, the primer is allowed to act for 3 minutes, excess solution is removed with paper tips and dried with a brief stream of air. Then gutta-percha tips together with the addition-crosslinking root-filling material RoekoSeal (Roeko, Germany) are introduced. The cavity is again sealed temporarily with Cavit (Espe, Germany). The RoekoSeal hardens. On the next day, the Cavit is removed, and the cavity can be filled with composite material. Even if the upper portion of the RoekoSeal filling is also milled away, the remainder of the silicone filling remains adhering in the root canal and cannot be inadvertently pulled out.

Example 4

Temporary Cementing of a Temporary Crown

A temporary finished crown of polycarbonate, which fits only approximately, is painted on its inside surface with a thin layer of the adhesive primer solution from Example 1, which adheres very well to this plastic according to PCT/EP 00/01042 and then is dried. The prepared stump of tooth onto which the temporary crown is to be applied temporarily is touched by adhesive primer solution only at a few points. DieFlex (Danville Materials, USA), a low-viscosity addition-crosslinking hard silicone which is normally used as a modeling silicone for the inlay technique in the direct method and which is pigmented in dental colors, is inserted into the finished, pretreated crown and placed on the stump. For two minutes, the hard silicone, now used as a cement, is fully cured. The excess can easily be removed with a hand instrument.

Example 5

Permanent Cementing of a (Permanent) Individual Crown

A metal ceramic individual crown which fits very well and is based on a chromium cobalt alloy in its metal part is also painted on its inside surface with a thin layer of the adhesive primer solution from Example 1, which adheres very well to non-noble metals according to PCT/EP 00/01042, and then dried. The prepared stump of tooth is then treated with the adhesive primer solution over the entire surface of the stump that is to be capped and is dried well. A medium-viscosity addition-crosslinking silicone known by the name Clearbite (Discus Dental, USA) is transparent but flows under pressure to yield extremely thin layers; it is normally used as a transparent bite impression casting material or as a transparent matrix for photocuring of composite restorations; this material is placed on the pretreated crown which is then placed on the stump. After three minutes, the hard silicone, used here as a cement, is fully cured. The excess is cautiously cut away at the edge of the crown. The crown sits very securely. The cement holds the crown elasticity to some extent, which can prevent splintering of ceramic and metal structure in the case of large point loads on ceramic crowns.

Example 6

Elastic Bone Cement

Two fresh rib bones of a swine are each cut perpendicularly on one end, ground obliquely at the edges approximately 3 mm of the horizontal edge with a rotating mill and then dried with pads. The cut and ground surfaces are then coated twice with thin layers of adhesive primer solution from Example 1 using a dental brush and then dried. Approximately 3 cm wide transparent film which is provided at the surface with two approx. 2 mm openings, is glued around the two parts of the ribs to be joined, which are held at a distance of 6 mm. The resulting space between the two rib parts is filled with the above-mentioned transparent addition-crosslinking silicone Clearbite by filling it with a static mixer and a so-called intraoral tip, such as those conventionally used for application for taking impressions in the field of dentistry, guiding it through the first opening to the bottom of the cavity to be filled, and from there filling with the compound until it runs out of the second opening. The space between the bone parts is filled in this way. The silicone cures within three minutes. After removing the adhesive film used as an aid, the two parts are joined elastically. Excess is removed with a scalpel. Storage in water at 40° C. does not show any weakening of the bond or elasticity even after four weeks.

The invention claimed is:

1. A method of treating natural teeth or bone with a kit of parts as an adhesive elastic material, which method comprises:
    applying to teeth or bone, sub-kit of parts 1, followed by applying sub-kit of parts 2, and
    subsequently allowing sub-kit of parts 2 to cure, wherein the kit of parts comprises:
    a) a copolymer having hydrogen-siloxane groups,
    b) a catalyst,
    c) a vinyl compound, and
    d) a hydrosilyl compound,
    wherein the copolymer having hydrogen-siloxane groups a) is a copolymer of siloxanes containing SiH groups with unsaturated compounds, or the copolymer having hydrogen-siloxane groups a) is a copolymer of unsaturated compounds onto which are grafted siloxanes having SiH groups, said kit further comprising two sub-kits of parts, whereby kit 1 contains:
    a) the copolymer having hydrogen-siloxane groups, and the sub-kit of parts 2 contains:
    b) the catalyst,
    c) the vinyl compound, and
    d) the hydrosilyl compound.

2. The method according to claim 1 as an adhesive root canal cement, wherein sub-kit of parts 2 is used in a second step after application of sub-kit of parts 1, and wherein sub-kit of parts 2 is subsequently allowed to cure.

3. The method according to claim 1 as an adhesive dental filling material, wherein sub-kit of parts 2 is used in a second step after application of sub-kit of parts 1, and wherein sub-kit of parts 2 is subsequently allowed to cure.

4. The method according to claim 1 as an adhesive elastic temporary dental filling material, wherein sub-kit of parts 2 is used in a second step after application of sub-kit of parts 1, and wherein sub-kit of parts 2 is subsequently allowed to cure.

5. The method according to claim 1 as an elastic bone filling material, wherein sub-kit of parts 2 is used in a second step after application of sub-kit of parts 1, and wherein sub-kit of parts 2 is subsequently allowed to cure.

6. The method according to claim 1 as an elastic bond, wherein sub-kit of parts 2 is used in a second step after application of sub-kit of parts 1, and wherein sub-kit of parts 2 is subsequently allowed to cure.

7. The method according to claim 1 as an adhesive elastic cement, wherein sub-kit of parts 2 is used in a second step after application of sub-kit of parts 1, and wherein sub-kit of parts 2 is subsequently allowed to cure.

8. The method according to claim 1 as an adhesive elastic temporary cement wherein sub-kit of parts 2 is used in a second step after application of sub-kit of parts 1, and wherein sub-kit of parts 2 is subsequently allowed to cure.

9. The method according to claim 1 as an elastic bracket adhesive, wherein sub-kit of parts 2 is used in a second step after application of sub-kit of parts 1, and wherein sub-kit of parts 2 is subsequently allowed to cure.

10. The method according to claim 1 as an elastic splint cement, wherein sub-kit of parts 2 is used in a second step after application of sub-kit of parts 1, and wherein sub-kit of parts 2 is subsequently allowed to cure.

11. The method according to claim 1 as an elastic bone cement, wherein sub-kit of parts 2 is used in a second step after application of sub-kit of parts 1, and wherein sub-kit of parts 2 is subsequently allowed to cure.

12. The method according to Claim 1 as an adhesive elastic sealing material, wherein sub-kit of parts 2 is used in a second step after application of sub-kit of parts 1 and wherein sub-kit of parts 2 is subsequently allowed to cure.

* * * * *